United States Patent
Payne

(10) Patent No.: US 7,047,999 B2
(45) Date of Patent: May 23, 2006

(54) HUMIDIFICATION CHAMBER WITH FLOAT-VALVE HAVING IMPROVED FLOAT

(75) Inventor: Simon Robert Payne, Milford (GB)

(73) Assignee: Intersurgical Limited, Wokingham (GB)

(*) Notice: Subject to any disclaimer, the term of this patent is extended or adjusted under 35 U.S.C. 154(b) by 150 days.

(21) Appl. No.: 10/446,759

(22) Filed: May 28, 2003

(65) Prior Publication Data
US 2004/0040599 A1 Mar. 4, 2004

(30) Foreign Application Priority Data
May 29, 2002 (GB) .................................. 0212375

(51) Int. Cl.
*F16K 31/18* (2006.01)

(52) U.S. Cl. ...................... 137/409; 137/430

(58) Field of Classification Search ............... 137/409, 137/426, 429, 430, 434, 448, 451
See application file for complete search history.

(56) References Cited

U.S. PATENT DOCUMENTS

| 4,448,213 A | * | 5/1984 | Seeley ...................... 137/448 |
| 5,426,271 A | * | 6/1995 | Clark et al. ............... 200/84 C |

FOREIGN PATENT DOCUMENTS

| AU | 468170 | 1/1976 |
| DE | 298620 A5 | 3/1992 |
| FR | 2602996 A | 2/1988 |
| GB | 1 589 102 | 5/1981 |

* cited by examiner

*Primary Examiner*—Kevin Lee
(74) *Attorney, Agent, or Firm*—Nixon Peabody LLP

(57) ABSTRACT

A method is disclosed for the manufacture of a float (30) comprising the following steps: providing a mould (10) having a first enclosure (12) opening into a second enclosure (14) of greater dimensions than the first enclosure (12), and an inlet (16) into the first enclosure (12), the first and second enclosures (12, 14) together defining the shape of the float (30); injecting a mixture comprising plastics material and blowing agent into the inlet (16), such that the mixture passes through the first enclosure (12) and then into the second enclosure (14); and causing or allowing the mixture to set, thereby forming the float (30). The float (30), the mould (10) and a fluid storage chamber (60) including the float (30) are also disclosed.

15 Claims, 3 Drawing Sheets

HUMIDIFICATION CHAMBER WITH FLOAT-VALVE HAVING IMPROVED FLOAT

Figure 1:
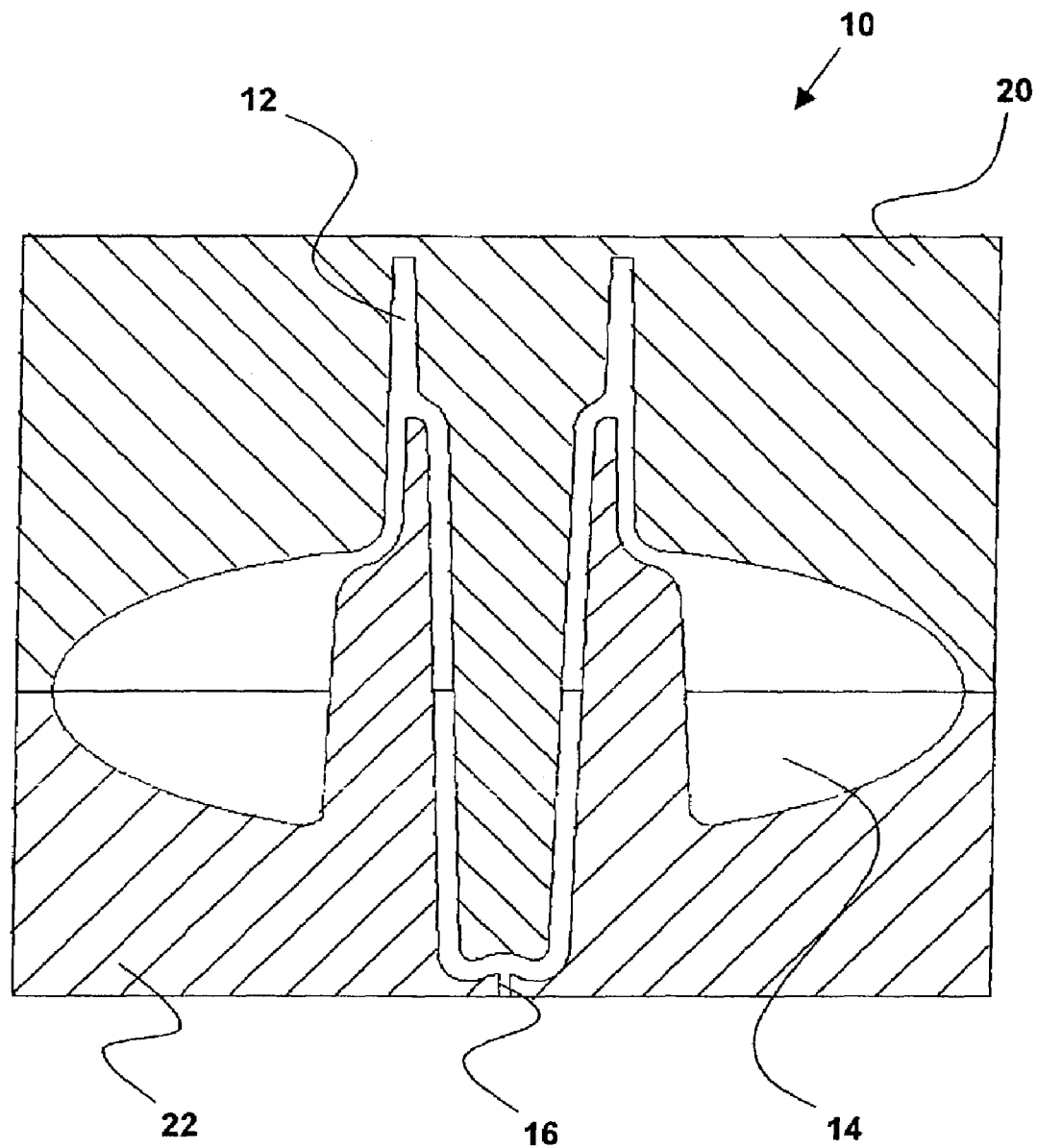

This invention relates to floats and methods for the manufacture of such floats, which are suitable, in particular, for controlling fluid levels in medical apparatus.

Floats have many fields of application and are widely used in float-valves which control fluid levels. In particular, float-valves have many medical applications such as maintaining the water level in a humidification chamber. Medical applications of float-valves often require floats that are exactly replicable, so that the water level maintained by separate float-valves is the same. This requirement may be critical in certain applications. Hence, a float for use in a float-valve must be replicable to an identical buoyancy and that buoyancy must be stable throughout the lifetime of the float.

Conventional floats are typically formed in plastics material and manufactured either by sealing two components, such as hollow hemispheres, together or blow moulding. These methods form a hollow inner chamber which gives the float its required buoyancy. It is generally desirable, in order to improve the buoyancy of the float, to produce a float with a low aspect ratio, which means that its width is significantly greater than its height.

Conventional floats having a hollow inner chamber providing buoyancy are susceptible to compression by an external pressure which would affect their buoyancy. Floats produced from two components are susceptible to leakage of water into the inner chamber through the join between the components, which would also affect buoyancy.

When using blow moulding, particularly when manufacturing floats of low aspect ratio, the final wall thickness will vary depending on the amount of extension that was required in each area of the wall in order to form the final shape of float from the initial shape of the plastics material, which is typically a cylinder. This results in areas of weakness in the float wall which may lead to shrinkage of the float in use and may present difficulties in replicating floats to the same buoyancy.

In certain applications, it is desirable to maximise the rigidity of the float whilst retaining sufficient float buoyancy. One such application is in a float-valve that maintains the water level in a humidification chamber forming part of a ventilation system. This is because the less compliant the float, the more accurate the ventilation of the patient. In general, however, it is difficult to manufacture conventional floats, such as those having a hollow inner chamber, that have both sufficient buoyancy and sufficient rigidity for use in a ventilation system.

Floats can also be manufactured using an alternative form of moulding, which uses a blowing agent mixed with the plastics material to form a float with many pockets of gas which give the float its necessary buoyancy. Floats manufactured using this method are easier to replicate than the aforementioned floats but suffer from the major disadvantage of being very expensive to manufacture due to the expense of the blowing agent.

There has now been devised an improved float and a method for the manufacture of such a float which overcomes or substantially mitigates the above-mentioned and/or other disadvantages of the prior art.

According to a first aspect of the invention, there is provided a method for the manufacture of a float comprising the steps of
a) providing a mould having a first enclosure opening into a second enclosure of greater dimensions than the first enclosure, and an inlet into the first enclosure, the first and second enclosures together defining the shape of the float;
b) injecting a mixture comprising plastics material and blowing agent into the inlet, such that the mixture passes through the first enclosure and then into the second enclosure; and
c) causing or allowing the mixture to set, thereby forming the float.

The method for the manufacture of a float according to the invention is advantageous primarily in that the reduction in pressure experienced by the mixture upon passing from the first enclosure to the larger second enclosure enhances the action of the blowing agent. This means that substantially less blowing agent is required, compared to conventional methods, to achieve the same reduction in density of the plastics material. Since blowing agent is expensive, this significantly reduces manufacturing costs.

The second enclosure is preferably of greater cross-sectional area than the first enclosure. By "cross-sectional area" is meant the area of the enclosure in the plane perpendicular to the direction of flow of plastics material during injection into the mould.

In the method of the invention, the mixture of plastics material and blowing agent is injected into the first enclosure. The first enclosure opens into the second enclosure at a junction between the first and second enclosures. The mixture flows from the first enclosure into the second enclosure, the first and second enclosures thus being respectively upstream and downstream of each other. As the mixture is injected into the mould, the mixture fills first the first enclosure and then the second enclosure, with the mixture advancing along a front through the first enclosure and then the second enclosure. The cross-sectional area of the first enclosure is preferably less than the cross-sectional area of the second enclosure. Furthermore, the cross-sectional area of the first enclosure is preferably relatively constant. More particularly, the cross-sectional area of the first enclosure is preferably of the same order of magnitude throughout substantially the whole extent of the first enclosure, by which is meant that the cross-sectional area varies by a factor of less than 10, more preferably less than 5, or less than 2, along a distance that corresponds to at least 70%, more preferably 80% or 90%, of the distance travelled by the advancing front of plastics material through the first enclosure.

The cross-sectional area of the second enclosure, on the other hand, preferably increases relatively rapidly from the junction of the first and second enclosures to a portion of the second enclosure with a peak cross-sectional area. The walls of the second enclosure preferably diverge relatively rapidly from the junction of the first and second enclosures with an initial angular separation of greater than 45°, are more preferably greater than 60°.

The ratio of the peak cross-sectional area of the second enclosure to the mean cross-sectional area of the first enclosure is typically in the range 10:1 to 1000:1, preferably 25:1 to 400:1, most preferably 65:1 to 225:1, for example approximately 100:1.

The plastics material may be any suitable plastics material and is preferably a polyolefin such as polypropylene. The mixture is preferably heated before injection into the mould, most preferably so that the plastics material is substantially molten, and the setting of the mixture is then preferably brought about by cooling.

A blowing agent is an additive well known in the art which releases gas to produce trapped bubbles of gas within the mixture, thereby giving the mixture a foam-like form.

The gas released is typically carbon dioxide. A suitable blowing agent may be obtained from Gabriel-Chemie Ges.m.b.H., Industriestraβe 1, A-2352 Gumpoldskirchen, Austria. The blowing agent is preferably an endothermic blowing agent which stops reacting below a certain temperature.

The majority of the mixture is preferably plastics material. The ratio, by weight, of plastics material to blowing agent is preferably in the range 65:35 to 99.5:0.5, more preferably 90:10 to 99.5:0.5, particularly 95:5 to 99.5:0.5, for example 99:1.

According to a second aspect of the invention, there is provided a mould for use in the manufacture of a float, the mould comprising a first enclosure opening into a second enclosure of greater dimensions than the first enclosure, and an inlet into the first enclosure.

The first and second enclosures are preferably dimensioned as described above. The first enclosure preferably comprises a portion which defines the walls of a hollow cylinder, preferably having a closed end. The second enclosure is preferably a spheroid shape, most preferably a generally prolate spheroid shape.

According to a third aspect of the invention, there is provided a float for inclusion in a float-valve, the float comprising a first portion of plastics material, and a second portion of plastics material having greater dimensions than the first portion, the first and second portions being integrally formed and at least the second portion containing pockets of trapped gas, wherein the second portion has a lower density than the first portion by virtue of a higher proportion of the volume of the second portion than the first portion being occupied by trapped gas pockets.

The float according to the third aspect of the invention is advantageous principally because the problems associated with floats having hollow inner chambers to provide buoyancy are removed. Such disadvantages include leakage of fluid into the chamber, shrinkage of the chamber during use, thereby affecting buoyancy, and the difficulty of producing floats of identical buoyancy. In addition, the float according to the invention may be formed with greater rigidity, whilst retaining sufficient buoyancy to function as a float, than is possible with conventional floats, such as those that have a single hollow chamber. This is particularly important in applications where greater float rigidity is desirable, such as in a float-valve that maintains the water level in a humidification chamber forming part of a ventilation system.

The ratio of the densities of the first and second portions is preferably in the range 85:15 to 55:45, more preferably 80:20 to 60:40 and most preferably 75:25 to 65:35, for example 70:30.

The first and second portions of the float preferably have dimensions corresponding to those described above for the first and second enclosures of the mould respectively. The first portion is preferably shaped so as to define a partially enclosed volume. The partially enclosed volume is preferably of generally cylindrical shape, with one closed end, and is preferably tapered. The second portion is preferably a spheroid, most preferably a generally prolate spheroid. Preferably, the partially enclosed volume extends through an opening in the second portion.

In a preferred embodiment, therefore, the float according to the invention comprises a first portion that is disposed centrally and is formed integrally with, and surrounded by, a second portion. The second portion has the form of a prolate spheroid and comprises plastics material of lower density than that of the first portion. Preferably, the first portion is disposed within an opening in the second portion.

The first portion preferably includes an operative part which is adapted to cooperate with a valve. The operative part is preferably a hollow cylinder which cooperates with a guide to control the alignment of the float. The guide may surround the hollow cylinder to constrain movement of the latter to movement along its longitudinal axis. The guide may thus have the form of a cylindrical tube within which the hollow cylinder is received.

According to a fourth aspect of the invention, there is provided a fluid storage chamber having a float-valve for controlling the level of a fluid within the chamber, the float-valve comprising a float according to the invention.

The float-valve preferably includes a valve cushion, preferably of elastomeric material, which can allow or prevent the inflow of fluid into the fluid storage chamber. The valve cushion is preferably received within the float, typically the operative part, and preferably cooperates with a fluid inlet to allow the inflow of fluid when the fluid is below a certain level and prevent the inflow of fluid when the fluid is at, or above, a certain level. The float-valve preferably has a guiding part which cooperates with the operative part of the float to maintain the float, in use, in a vertical orientation.

In the majority of applications, the fluid will be water or an aqueous medium.

Figure 2:
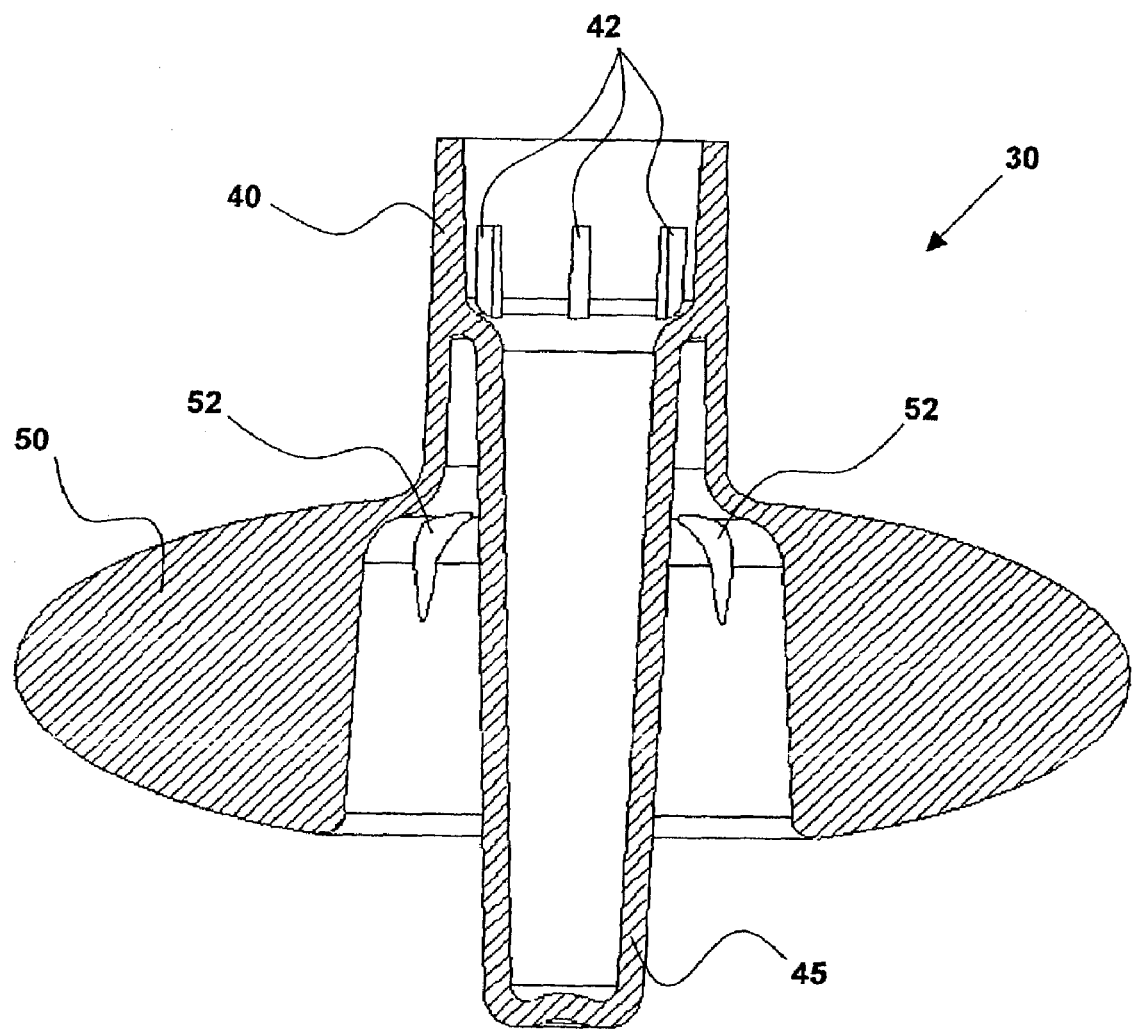
Figure 3:
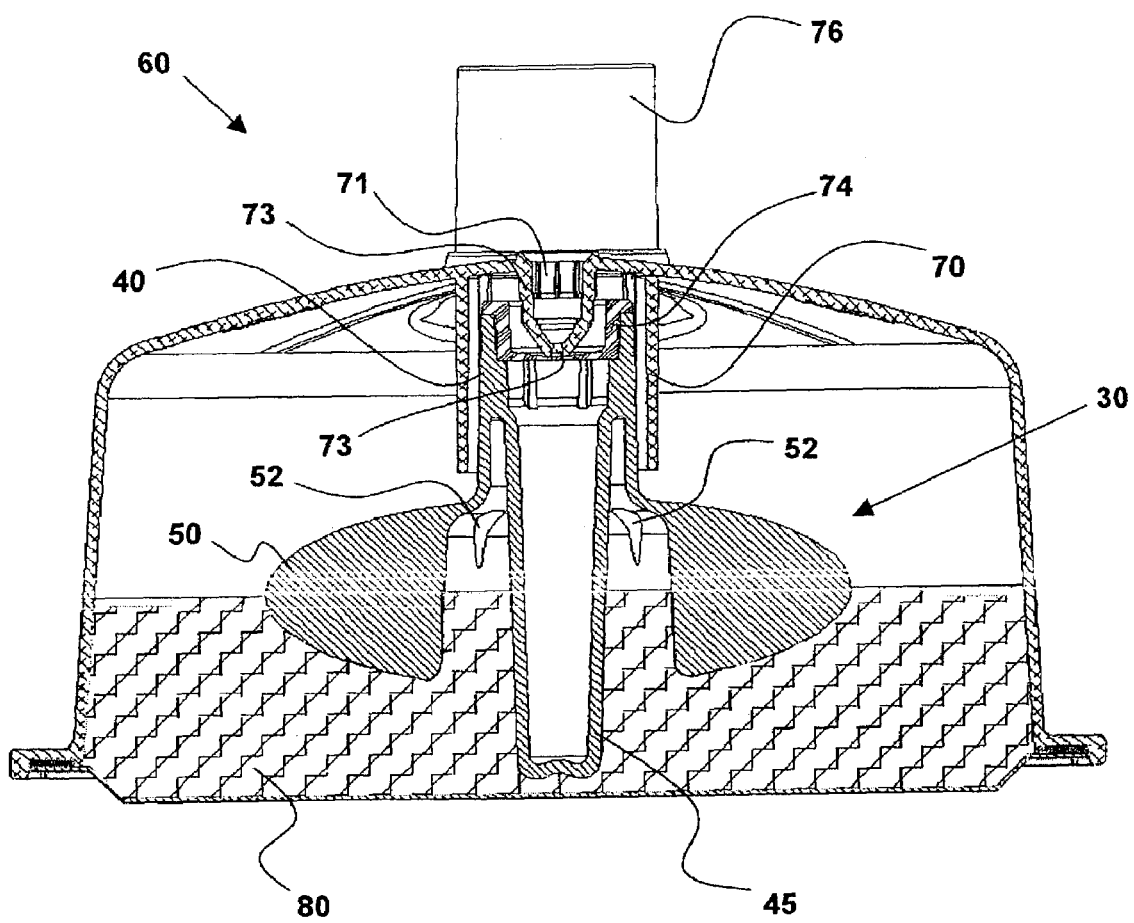

The invention will now be described in greater detail, by way of example only, with reference to the accompanying drawings, in which FIG. 1 is a sectional view through a typical mould for a method for the manufacture of a float according to the present invention;

FIG. 2 is a diametrical section through a float according to the present invention; and FIG. 3 is a sectional view of a fluid storage chamber according to the present invention.

Referring firstly to FIG. 1; a presently preferred mould, for use in a method for the manufacture of a float according to the present invention, is generally designated 10. A method for the manufacture of a float according to the present invention requires a mould 10 having a first enclosure 12, a second enclosure 14 of greater dimensions than the first enclosure 12 and an inlet 16 into the first enclosure 12.

The presently preferred mould 10 comprises an upper part 20 and a lower part 22, which are able to engage so as to define the first enclosure 12 and the second enclosure 14, as shown in FIG. 1. The lower part 22 includes the inlet 16 into the first enclosure 12. The first enclosure 12 and second enclosure 14 are shaped so as to form a float with a shape as shown in FIG. 2 and described later. All relevant surfaces of this are tapered so as to allow the upper and lower parts 20,22 of the mould 10 to disengage once the float is formed so that the float may be removed from the mould 10.

Firstly, the upper and lower parts 20,22 of the mould 10 are engaged to define the first and second enclosures 12,14, which are sealed from the exterior of the mould 10 save for the inlet 16.

Next, a plastics material and a blowing agent are mixed and heated to form a moulding mixture. The plastics material is typically a polyolefin such as polypropylene. The blowing agent may be any suitable blowing agent. Examples of suitable blowing agents are those supplied by Gabriel-Chemie Ges.m.b.H., Industriestraβe 1, A-2352 Gumpoldskirchen, Austria. The blowing agent is typically an endothermic blowing agent which stops reacting below a certain temperature.

The ratio of plastics material and blowing agent present in the mixture will vary depending on the density, and hence buoyancy, of float required. However, there will generally be a major proportion of plastics material and a minor proportion of blowing agent. A typical ratio is 19 parts polypropylene to 1 part blowing agent, by weight. The blowing agent acts to form many bubbles of gas, typically carbon dioxide, within the moulding mixture, thereby giving the moulding mixture a foam-like form.

Next, the heated moulding mixture is injected, under pressure, through the inlet 16 and into the first enclosure 12. The moulding mixture flows through the first enclosure 12, still under pressure, and into the second enclosure 14. As the moulding mixture enters the second enclosure 14, the pressure of the moulding mixture falls dramatically, causing the bubbles of gas within the moulding mixture to expand significantly. Injection into the mould 10 is continued until the first and second enclosures 12,14 are fully charged.

The mould 10 is cooled such that upon contacting the walls of the second enclosure 14, the moulding mixture solidifies and forms a continuous "skin". Within the body of the mixture the elevated temperature persists for a longer period, allowing the blowing agent to react. Once the moulding mixture has cooled sufficiently, the upper and lower parts 20,22 of the mould are disengaged and the float is removed.

Turning now to FIG. 2, a float according to the present invention is generally designated 30. The float 30 is formed by injection moulding a mixture of plastics material and blowing agent, as described above. The float 30 comprises an upper portion 40, an inner float body 45 and an outer float body 50, which are all integrally formed in the injection moulding process.

The upper portion 40 is a generally cylindrical tube with relatively thin walls and a diameter that increases gradually and slightly from an open upper end to a open lower end (as viewed in FIG. 2). The upper portion 40 includes six upright rectangular openings 42 in the wall of the cylinder at equiangularly spaced positions.

The inner float body 45 is a generally cylindrical tube that depends downwardly, internally of the upper portion 40. The inner float body 45 has a diameter that reduces gradually and slightly from an open upper end to a closed lower end (as viewed in FIG. 2). The inner float body 45 has a wall thickness similar to that of the upper portion 40. The upper end of the inner float body 45 has an outwardly extending curved lip which extends into the interior wall of the upper portion 40, immediately below the openings 42.

The outer float body 50 is a solid prolate spheroid with a generally cylindrical central opening, through which the inner float body 45 extends. The opening has a diameter greater than that of the upper portion 40 and which gradually and slightly increases from its upper end to its lower end (as viewed in FIG. 2). The lower end of the upper portion 40 has an outwardly extending curved lip which extends into the outer float body 50 at the upper end of the cut-away portion. The lower end of the inner float body 45 extends beyond the lower end of the cut-away portion. In addition, the outer float body 50 includes six openings 52, at equiangularly spaced positions, close to the upper portion of the central opening.

The plastics material of the outer float body 50 has a foam-like structure with many pockets of gas trapped within the plastics material of the outer float body 50. Typically, the method for the manufacture of a float according to the invention causes the outer float body 50 to be approximately 60% less dense than an identical volume of the same plastics material.

Turning now to FIG. 3, a fluid storage chamber having a float-valve, according to the present invention, is generally designated 60. The roof of the fluid storage chamber 60 is formed with a centrally positioned and downwardly extending nozzle 72 having an inlet 71 in the roof of the fluid storage chamber 60, and a smaller opening 73 at the lower end of the nozzle 72. The nozzle 72 communicates with a fluid source 76 through inlet 71. The roof of the fluid storage chamber 60 further includes a centrally positioned and downwardly extending guiding sleeve 70 of cylindrical shape which is of greater diameter than the nozzle 72.

The fluid storage chamber 60 includes a float 30 according to the present invention which is a component of the float-valve. The float 30 is located within the fluid storage chamber 60 such that the lower end of the inner float body 45 rests on the base of the fluid storage chamber 60, and the majority of the upper portion 40 of the float 30 is received by the guiding sleeve 70.

A valve cushion 74, which is typically formed from elastomeric material, has the form of a cup and is received within the open upper end of the upper portion 40 of the float 30. The open upper end of the valve cushion 74 has an outwardly extending flange. The flange of the valve cushion 74 supports the valve cushion 74 on the rim of the upper portion 40 of the float 30, such that the base of the valve cushion 74 lies immediately below opening 73 of the nozzle 72.

In use, the fluid source supplies fluid 80 through opening 73. The fluid 80 fills the valve cushion 74, and flows down the exterior of the float 30 and onto the base of the fluid storage chamber 60. The fluid storage chamber 60 begins to fill with fluid 80. The openings 52 in the float 30 prevent air becoming trapped between the inner and outer float bodies 45,50 and affecting the buoyancy of the float 30. When the fluid 80 reaches a certain level, the float 30 is lifted by the buoyancy of the inner and outer float bodies 45,50. The float 30 is held in an upright position by the guiding sleeve 70. The float 30 will continue to rise until the fluid 80 reaches a sufficient level for the valve cushion 74 to be forced against the outlet opening 73 with enough force to prevent the inflow of fluid 80 through the opening 73. The fluid 80 will therefore be prevented from entering the fluid storage chamber 60 until the level of fluid 80 falls, thereby removing the valve cushion 74. from the opening 73.

The invention claimed is:

1. A humidification chamber having a float-valve for controlling the level of a fluid within the chamber, the float-valve including a float comprising a first portion of plastics material, and a second portion of plastics material having greater dimensions than the first portion, the first and second portions being integrally formed and at least the second portion containing pockets of trapped gas, wherein the second portion has a lower density than the first portion by virtue of a higher proportion of the volume of the second portion than the first portion being occupied by trapped gas pockets.

2. A humidification chamber as claimed in claim 1, wherein the first and second portions have a first and second density respectively, and the ratio of the first and second densities is in the range 85:15 to 55:45.

3. A humidification chamber as claimed in claim 1, wherein the second portion is of greater cross-sectional area than the first portion.

4. A humidification chamber as claimed in claim 1, wherein the first portion joins the second portion at a junction between the first and second portions, and the second portion has walls that diverge from the junction of the first and second portions with an initial angular separation of greater than 45°.

5. A humidification chamber as claimed in claim 1, wherein the second portion has a cross-sectional area that increases from the junction of the first and second portions to a portion of the second portion with a peak cross-sectional area, the first portion has a mean cross-sectional area, and the ratio of the peak cross-sectional area of the second portion to the mean cross-sectional area of the first portion is in the range 10:1 to 1000:1.

6. A humidification chamber as claimed in claim 1, wherein the first portion is disposed centrally and is formed integrally with, and surrounded by, the second portion, and the second portion has the form of a prolate spheroid and comprises plastics material of lower density than that of the first portion.

7. A humidification chamber as claimed in claim 1, wherein the first portion includes an operative part which is adapted to cooperate with a valve.

8. A humidification chamber as claimed in claim 7, wherein the operative part is a hollow cylinder which cooperates with a guide to control the alignment of the float.

9. A humidification chamber having a float-valve for controlling a level of a fluid within the chamber, the float-valve including a float comprising a first portion of plastics material and a second portion of plastics material having greater dimensions than the first portion, the first and second portions being integrally formed and at least the second portion containing pockets of trapped gas, wherein the first portion includes a generally cylindrical tube adapted to cooperate with a valve and a guiding sleeve of the float-valve, the guiding sleeve constraining movement of the generally cylindrical tube, in use, to movement along its longitudinal axis, and the second portion has a lower density than the first portion by virtue of a higher proportion of the volume of the second portion than the first portion being occupied by trapped gas pockets.

10. A humidification chamber as claimed in claim 9, wherein the float-valve includes a valve cushion which can allow or prevent inflow of fluid into the humidification chamber.

11. A humidification chamber as claimed in claim 10, wherein the valve cushion is received within the generally cylindrical tube of the float and cooperates with a fluid inlet to allow the inflow of fluid when the fluid is below a certain level and prevent the inflow of fluid when the fluid is at, or above, a certain level.

12. A humidification chamber as claimed in claim 11, wherein the first and second portions have a first and second density respectively, and the ratio of the first and second densities is in the range 85:15 to 55:45.

13. A humidification chamber as claimed in claim 11, wherein the second portion is of greater cross-sectional area than the first portion.

14. A humidification chamber as claimed in claim 11, wherein the first portion joins the second portion at a junction between the first and second portions, and the second portion has walls that diverge from the junction of the first and second portions with an initial angular separation of greater than 45°.

15. A humidification chamber as claimed in claim 11, wherein the second portion has a cross-sectional area that increases from the junction of the first and second portions to a portion of the second portion with a peak cross-sectional area, the first portion has a mean cross-sectional area, and the ratio of the peak cross-sectional area of the second portion to the mean cross-sectional area of the first portion is in the range 10:1 to 1000:1.

* * * * *